United States Patent [19]

Walser

[11] Patent Number: 5,432,176

[45] Date of Patent: Jul. 11, 1995

[54] METHOD OF RETARDING THE PROGRESSION OF CHRONIC RENAL FAILURE

[75] Inventor: Mackenzie Walser, Ruxton, Md.

[73] Assignee: The John Hopkins University, Baltimore, Md.

[21] Appl. No.: 996,757

[22] Filed: Dec. 24, 1992

Related U.S. Application Data

[63] Continuation-in-part of Ser. No. 277,161, Nov. 29, 1988, Pat. No. 5,175,144.

[51] Int. Cl.$^6$ .................. A61K 31/495; A61K 31/50; A61K 37/00; A61K 31/56
[52] U.S. Cl. ........................... 514/252; 514/2; 514/11; 514/171; 514/289; 514/327
[58] Field of Search ............... 514/2, 11, 179, 252, 514/282, 289, 327, 171

[56] References Cited

U.S. PATENT DOCUMENTS

| | | | |
|---|---|---|---|
| 3,714,159 | 1/1973 | Janssen et al. | 424/601 |
| 4,107,306 | 8/1978 | Voorhees | 514/171 |
| 4,320,146 | 3/1982 | Walser | 424/601 |

FOREIGN PATENT DOCUMENTS 2116425 9/1983 United Kingdom .

OTHER PUBLICATIONS

Remington's Pharmaceutical Sciences, 16th edition, 1980, pp. 1858–1859.

M. Moguilewsky, et al., "RU 38486: Potent Antiglucocorticoid Activity Correlated with Strong Binding to the Cytosolic Glucocorticoid Receptor Followed by anImpaired Activation", *S. Steroid Biochem*, vol. 20, No. 1, pp. 271–276 (1984).

Roland M. Schaefer, et al., "Evidence for Reduced Catabolism by the Antiglucocorticoid RU 38486 in Acutely Uremic Rats", *Am. J. Nephrol*, 7, pp. 127–131 (1987).

Xavier Bertagna, et al., "The New Steroid Analog RU 486 Inhibits Glucocorticoid Action in Man", *Journal of Clinical Endocrinology and Metabolism*, vol. 59, No. 1, pp. 25–28 (1984).

N. Gretz, et al., "Low-proteindiet supplemented by keto acids in chronic renal failure: A prospective controlled study", *Kidney International*, vol. 24, Suppl. 16 (1983), pp. S-263-S-267.

M. Walser, "Ketoacids in the treatment of uremia*", *Clinical Nephrology*, vol. 3 No. 5 (1975).

G. Barsotti, et al., "Effects on Renal Function of a Low–Nitrogen Diet Supplemented with Essential Amino Acids and Ketoanalogues and of Hemodialysis and Free Protein Supply in Patients with Chronic Renal Failure", *Nephron* 27:113–117 (1981).

W. E. Mitch, et al., "The Effect of Keto Acid–Amino Acid Supplement to Restricted Diet on the Progression of Chronic Renal Failure", *The New England Journal of Medicine*, 311:623–629 (Sep. 6), 1984.

J. Burns, et al., "Comparison of the effects of keto acid analogues and essential amino acids on nitrogen homeostasis in uremic patients on moderately protein-restricted diets", *The American Journal of Clinical Nutrition 31*: Oct. 1978, pp. 1767–1775.

M. Walser, et al., "Progression of chronic renal failure in patients given ketoacids following amino acids", *Kidney International*, vol. 32 (1987), pp. 123–128.

Nieman, et al., "Clinical Applications of the Glucocorticoid and Progestin Atnagonist RU 486," appearing in *Receptor Mediated Antisteroid Action*/Editor M. K. Agarwal (1987).

(List continue on next page.)

*Primary Examiner*—Raymond Henley, III
*Attorney, Agent, or Firm*—Panitch Schwarze Jacobs & Nadel

[57] ABSTRACT

Progression of chronic renal failure can be retarded or arrested by administering to humans suffering from such disorder an agent which suppresses the production of glucocorticoids in the human together with a glucocorticoid. An example of an agent which suppresses the production of glucocorticoids includes ketoconazole. Exemplary of the glucocorticoid is prednisone.

16 Claims, 1 Drawing Sheet

OTHER PUBLICATIONS

Gagne, et al., "RU38486: A Potent Antiglucocorticoid in Vitro and In Vivo," *J. Steriod Biochem*, vol. 23, No. 3, pp. 247-251 (1985).

Mitch, et al., "Long-Term Effects of a New Ketoacid-Amino Acid Supplement in Patients with Chronic Renal Failure," *Kidney International*, 22:48-53 (1982).

Pende, et al., "Evaluation of the Effects Induced by Four Opiate Drugs, with Different Affinities to Opioid Receptor Subtypes, on ANterior Pituitary LH, TSH, PRL and GH Secretion and on Cortisol Secretion in Normal Men," *Biomedicine & Pharmacotherapy*, 1986, 40, 178-182.

Aggernaes, et al., "The Effect of Sodium Valproate on Serum Cortisol Levels in Healthy Subjects and Depressed Patients," *Acta Psychiatr. Scand.* 1988:77:170-174.

Lechin, et al., "Role of Stress in the Exacerbation of Chronic Illness: Effects of Clonidine Administration on Blood Pressure and Plasma Norepinephrine, Cortisol, Growth Hormone and Prolactin Concentrations," *Psychoneuroendocrinology, vol. 12, No. 2 pp. 117-129 (1987)*.

Stubbs, et al., "Hormonal and Metabolic Responses to an Enkephalin Analogue in Normal Man," *The Lancet*, Dec. 9, 1978, pp. 1225-1227.

J. J. Legros, et al., "Confirmation of the Inhibitory Influence of Exogenous Oxytocin on Cortisol and ACTH in Man: Evidence of Reproducibility", *Acta Endocrinologica*, 114: pp. 345-349 (1987).

Farwell, et a., "Total Suppression of Cortisol Excretion by Ketoconazole in the Therapy of the Ectopic Adrenocorticotropic Hormone Syndrome", *The American Journal of Medicine*, vol. 84 (Jun. 1988), pp. 1063-1066.

Stowinski-Srzednicka, et al., "Effect of Clonidine on Beta-Endorphin, ACTH and Cortisol Secretion in Essential Hypertension and Obesity," *Eur. J. Clin. Pharmacol* (1988) 35:115-121.

Jonathan R. Diamond, M.D., "Physiology and Cell Biology Update—The Role of Reactive Oxygen Species in Animal Models of Glomerular Disease," *Am Journal of Kidney Diseases XIX.* No. 3, pp. 292-300 (1992).

Satoru Matsusue et al., "Healing of Intestinal Anastomoses in Adrenalectomized Rats Given Corticosterone," *Am. J. Physiol. 263*, pp. R164-R168 (1992).

J. M. Villette et al., "Circadian Variations in Plasma Levels of Hypophyseal, Adrenocortical and Testicular Hormones in Men Infected with Human Immunodeficiency Virus," Journal of Clinical Endocrinology & Metabolism 70, pp. 572-577 (1990).

Mackenzie Walser et al., "Progression of Chronic Renal Failure on Substituting a Ketoacid Supplement for an Amino Acid Supplement," *J. Am. Soc. Nephrol.*, 2, pp. 1178-1185 (1992).

B. Ulrich et al., "Pharmacokinetics/Pharmacodynamics of Ketoconazole-Prednisolone Interaction," *J. Pharmacol. Exp. Ther. 260*, No. 2, pp. 487-490 (1992).

Helen Wiseman et al., "The Antioxidant Action of Ketoconazole and Related Azoles: Comparison with Tamoxifen and Cholesterol," *Chem.-Biol. Interactions* 79, pp. 229-243 (1991).

T. Taylor, et al., "B-Endorphin Suppresses Adrenocorticotropin and Cortisol Levels in Normal Human Subjects", *Journal of Clinical Endocripology and Metabolism*, vol. 57, No. 3, pp. 592-596 (1983).

B. Ambrosi, et al., "Loperamide, and Opiate Analogue, Inhibits Plasma Acth Levels in Patients with Addison's Disease", *Clinical endocrinlogy*, 24, pp. 483-489 (1986).

G. Teutsch, et al., "17a-Alkynyl-11b, 17-Dihydroxyandrostane Derivatives: A New Class of Potent Glucocortincoids.", *Steriods*, vol. 38, No. 6, pp. 651-665 (1981).

Beverley E. Pearson, et al. "Response To Steriod Suppression In Major Depression Resistant To Antidepressant Therapy", *Journal of Clinical Psychopharmacology*, vol. 11/No. 2, Apr. 1991.

5,432,176

METHOD OF RETARDING THE PROGRESSION OF CHRONIC RENAL FAILURE

CROSS-REFERENCE TO RELATED APPLICATION

This application is a continuation-in-part of application Ser. No. 07/277,161, filed Nov. 29, 1988, now U.S. Pat. No. 5,175,144.

FIELD OF THE INVENTION

This invention relates to therapeutic treatment of humans suffering from chronic renal failure. More particularly, the invention is directed to the administration to such humans of compositions which retard or arrest the progression of such failure.

BACKGROUND OF THE INVENTION

Since the first anecdotal evidence that nutritional therapy may slow the progression of chronic renal failure (see Walser M., "Ketoacids in the Treatment of Uremia," *Clinical Nephrology*, 3:180–187 (1975)), there has been growing interest in two possibilities: (1) that a common mechanism causes progression of many types of chronic renal failure, and (2) that this process can be slowed or arrested by diet or drugs.

Many mechanisms of progression have been postulated, based on experiments in animals and/or clinical observations. Factors proposed to contribute to progression include arterial pressure, and more specifically, glomerular capillary pressure which is reduced by angiotensin-converting enzyme inhibitors; serum calcium times phosphorus product; urinary phosphorus excretion; protein intake itself; hyperuricemia; hypertriglyceridemia; hypercholesterolemia; and hyperoxalemia.

Ketoacid mixtures, administered in conjunction with a low protein, low phosphorus diet, have been reported to slow progression in several studies, see Mitch, W. E., et al., "The Effect of a Keto Acid-Amino Acid Supplement to a Restricted Diet on the Progression of Chronic Renal Failure," *New England Journal of Medicine*, 311:623–629 (1984); Gretz, N., et al., "Low-Protein Diet Supplemented by Ketoacids in Chronic Renal Failure: A Prospective Study," *Kidney International*, 24, Suppl. 16:S263–S267 (1983); and Barsotti, G., et al., "Effects on Renal Function of a Low-Nitrogen Diet Supplemented with Essential Amino Acids and Keto Analogs and of Hemodialysis and Free Protein Supply in Patients with Chronic Renal Failure," *Nephron* 27:113–117 (1981), but see Burns, J, et al., "Comparison of the Effects of Ketoacid Analogs and Essential Amino Acids on Nitrogen Homeostasis in Uremic Patients on Moderately Protein-Restricted Diets," *American Journal of Clinical Nutrition*, 31:1767–1775 (1978).

However, in most of these reports, no attempt was made to differentiate between the effects of the diet and the ketoacids. More recently, it has been reported that some patients progressing on this diet supplemented with essential amino acids exhibit slowed or arrested progression when changed to ketoacids, suggesting a specific effect of ketoacids on progression, see Walser, M , et al., "Progression of Chronic Renal Failure on Substituting a Ketoacid Supplement for an Amino Acid Supplement," *J. Amer. Soc. Nephrol.*, 2:1178–1185 (1992). However, in these studies, compliance with a restrictive diet was required.

Although much research has been done, a need still exists for treatment methods which retard, i.e., slow or arrest, the progression of chronic renal failure and do not require dietary compliance.

SUMMARY OF THE INVENTION

An aspect of the present invention is a method of retarding or arresting the progression of chronic renal failure in humans by administering an effective amount of an agent which suppresses the daily peaks in production of glucocorticoids together with a sufficient amount of a glucocorticoid to prevent glucocorticoid deficiency.

BRIEF DESCRIPTION OF THE DRAWINGS

The forgoing summary, as well as the detailed description of the preferred embodiments, will be better understood when read in conjunction with the appended drawing.

DETAILED DESCRIPTION OF THE PREFERRED EMBODIMENT

Figure 1B:
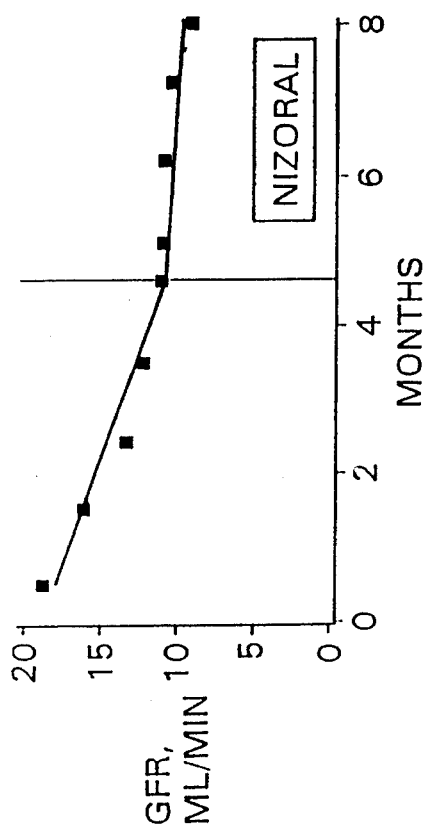
FIG. 1 comprises FIGS. 1A through 1D and shows the glomerular filtration rates of patients against time before and after treatment by the method of the invention.

An aspect of the present invention is a method whereby the progression of chronic renal failure in humans (or other animals) may be retarded or arrested by administering to humans suffering from such disorders an effective amount of an agent which suppresses the daily peaks in production of glucocorticoids together with a low dose of a glucocorticoid.

Agents believed to be useful in the present invention include drugs which suppress the production of glucocorticoids. Preferably, the glucocorticoid dose administered together with the suppressor is somewhat less than the replacement dose level. Replacement dose level is the dose that achieves an average normal level of glucocorticoid function when administered chronically to adrenalectomized subjects.

The following agents which are known to suppress glucocorticoid production in humans would appear to be useful when administered together with a glucocorticoid according to the present invention in retarding the progression of chronic renal failure:

(1) Ketoconazole: This is an antifungal agent found to inhibit adrenocortical glucocorticoid production profoundly or even completely. Farwell, A. P., et al., "Total Suppression of Cortisol Excretion by Ketoconazole in the Therapy of the Ectopic Adrenocorticotropic Hormone Syndrome," *The American Journal of Medicine*, 84:1063–1066 (1988). Recently, ketoconazole has been reported to prolong the half-life of the glucocorticoid prednisolone ($\Delta^1$-hydrocortisone). B. Ulrich et al., "Pharmacokinetics/Pharmacodynamics of Ketoconazole-Prednisolone Interaction," *The Journal of Pharmacology and Experimental Therapeutics*, 260:487–490 (1992).

(2) Sodium valproate: This is an anticonvulsant, widely used, but not without serious side effects and toxicity. It has been shown to reduce serum cortisol levels by more than fifty percent within a few hours in normal subjects. Aggernaes, H. et al., "The Effect of Sodium Valproate on Serum Cortisol Levels in Healthy Subjects and Depressed Patients," *Acta Psychiatr. Scand.*, 77:170–174 (1988).

(3) Enkephalins: These pentapeptides and their synthetic analogs, notably "DAMME" ([D-ala$^2$, Me- Phe[4], Met(O)-ol] enkephalin), reduce cortisol levels acutely in man. Stubbs, W. A., et al., "Hormonal and Metabolic Responses to an Enkephalin Analog in Normal Man," *The Lancet,* 1978:1225-1227 (Dec. 9, 1978); and Taylor, T., "Beta-Endorphin Suppresses Adrenocorticotropin and Cortisol Levels in Normal Human Subjects,'-'*Journal of Clinical Endocrinology and Metabolism,* 57:592-596 (1983).

(4) Opioids: Alkaloids like morphine also interact with the same or similar receptors as enkephalins. Opioids shown to decrease cortisol levels in man include morphine, pentazocine, nalorphine and buprenorphine. Pende, A., et al., "Evaluation of the Effects Induced by Four Opiate Drugs, with Different Affinity to Opioid Receptor Subtypes, on Interior Pituitary LH, TSH, PRL and GH Secretion and on Cortisol Secretion in Normal Man, "*Biomed Pharmacother.,* 40:178-182 (1986). Chronic administration of these may not be practical owing to side effects and/or addictive properties. However, loperamide, commercially available under the trademark "IMODIUM" from Janssen Pharmaceutica, N.V., is not addictive, but does suppress adrenocorticotrophic hormone production. See Ambrosi, B., et al, "Loperamide, an Opiate Analog, Inhibits Plasma ACTH Levels in Patients with Addison's Disease,"*Clinical Endocrinology,* 24:483-489 (1986). Loperamide and similar butyramides are described in Janssen, et al. U.S. Pat. No. 3,714,159.

(5) Clonidine: This widely used anti-hypertensive drug has recently been shown to lower cortisol levels in man. See Slowinska-Srzednicka, J., et al., "Effect of Clonidine on Beta-Endorphin, ACTH and Cortisol Secretion in Essential Hypertension and Obesity," *European Journal of Clinical Pharmacology,* 35:115-121 (1988); and Lechin, F., et al. "Role of Stress in the Exacerbation of Chronic Illness: Effects of Clonidine Administration on Blood Pressure and Plasma Norepinephrine, Cortisol, Growth Hormone and Prolactin Concentrations," *Psychoneuroendocrinology,* 12:117-129 (1987). Clonidine is already commonly used to treat hypertension in patients with chronic renal failure.

(6) Oxytocin: Intravenous infusion of this hormone (widely used to induce labor) lowers cortisol levels in normal men. Legros, J. J., et al. "Confirmation of the Inhibitory Influence of Exogenous Oxytocin on Cortisol and ACTH in Man: Evidence of Reproducability," *ACTA Endocrinologica,* 114:345-349 (1987). Oxytocin can be given as an intranasal spray, and side effects are minor.

Glucocorticoids are steroid hormones which modify certain metabolic reactions and have an anti-inflammatory effect. Endogenous glucocorticoids are produced by the adrenal cortex and influence carbohydrate, fat and protein metabolism and are also known to affect muscle tissue, the nervous system and the circulatory system. Glucocorticoids produced by the human adrenal gland include cortisol, corticosterone, 11-deoxycortisol, 11-deoxycorticosterone, aldosterone, 18-hydroxycorticosterone and 18-hydroxy, 11-deoxycorticosterone. In humans, cortisol (also known as hydrocortisone) is the most abundantly produced. Many analogs of hydrocortisone, such as prednisone ($\Delta^1$-dehydrocortisone) and prednisolone ($\Delta^1$-hydrocortisone) are available commercially.

Glucocorticoids play a role in the regulation of protein turnover. They are often used therapeutically in chronic renal disease. U.S. patent application Ser. No. 07/277,161, filed Nov. 29, 1988, discloses that suppression of the endogenous production of glucocorticoids or blocking of their binding to receptors slows or arrests the progression of chronic renal failure. While the Applicant does not wish to be bound by any particular theory, ketoconazole may slow progression by suppression of diurnal cortisol peaks or an antioxidant effect. See H. Wiseman et al., "The Antioxidant Action of Ketoconazole and Related Azoles: Comparison with Tamoxifen and Cholesterol,"*Chem.-Biol. Interactions,* 79:229-243 (1991). There is considerable evidence for oxidant injury as the cause of progression. See review of J. R. Diamond, "The Role of Reactive Oxygen Species in Animal Models of Glomerular Disease," *Am. J. Kidney Dis.,* 19:292-300 (1992).

Unexpectedly, in the present invention, it has been found that administration of a glucocorticoid suppressor together with a glucocorticoid is more effective than administration of a suppressor alone in retarding or arresting the progression of chronic renal failure. Suppression of glucocorticoid action through suppression of production entails the possibility of excessive suppression, thereby causing glucocorticoid insufficiency. In the present invention, a glucocorticoid suppressor is administered together with a glucocorticoid where, preferably, the dose of glucocorticoid is chosen to be somewhat less than the "replacement dose level." Thus, if the suppressor were totally effective in suppressing adrenocortical production of glucocorticoids, and if it had no effects on glucocorticoid metabolism or on glucocorticoid interaction with the glucocorticoid receptors, a low level of glucocorticoid function would still be present.

Administration can be oral or parenteral. It is believed that the appropriate dosages of the glucocorticoid suppressor could be readily ascertained from the scientific literature cited herein.

For example, with respect to ketoconazole, appropriate dosages are discussed in Farwell et al., supra. A dosage of 200-400 mg/day suppresses glucocorticoid production to a mild degree.

Aggernaes et al., supra, discloses that an 800 mg dosage of sodium valproate administered by intravenous injection suppressed serum cortisol levels in normal subjects. According to the *Physicians' Desk Reference,* 44th Edition, pp. 513-515 (1990), the usual daily dose of valproate is 10 mg/kg/daily and the maximum recommended dosage is 60 mg/kg/daily.

With regard to enkephalins, appropriate dosages for use in conjunction with the present methods are suggested in Stubbs et al., supra, and Taylor, supra.

The only known opioid which may be administered on a long-termbasis without danger of addiction is loperamide. Concurrent use of a laxative would be required. Accordingly to Ambrosi et al., supra, an oral dosage of 16 mg produced a decrease in plasma adrenocorticotropic hormone levels. According to the *Physicians' Desk Reference,* supra, at pp. 1083-1084, the daily dosage of loperamide should not exceed 16 mg.

A daily dosage of clonidine ranging from 0.2 mg-0.6 mg suppresses cortisol levels as discussed in Slowinski-Srzednicka et al., supra, and Lechin et al., supra.

Appropriate dosages of oxytocin are suggested in Legros et al., supra.

Preferably, in the method of the present invention, the glucocorticoid suppressor is ketoconazole and the glucocorticoid is prednisone. As mentioned above, ketoconazole is now known to inhibit prednisone metabolism. Hence, a given dose of prednisone exerts a greater glucocorticoid effect in the presence of ketaconazole. The more slowly ketoconazole is metabolized in a given patient (thereby causing relatively more adrenocortical suppression), the more slowly prednisone will be metabolized, thus overcoming possible glucocorticoid insufficiency. This combination of drugs tends to "clamp" glucocorticoid function at a low, but adequate, level preventing glucocorticoid insufficiency.

Another possible benefit of the glucocorticoid clamp of the method of the present invention is that diurnal variations in glucocorticoid levels are blunted or eliminated. These variations are about five-fold in normal subjects, but their function, if any, is unknown. While the Applicant does not wish to be bound by any particular theory, the peaks of glucocorticoid levels during each day, as well as peaks occurring from day to day in response to various stimuli including stress, may be particularly damaging to renal function by impairing the healing process. It is known that sustained high levels of glucocorticoids impair healing. See S. Matsusue et al., "Healing of Intestinal Anastomoses in Adrenalectomized Rats Given Corticosterone," *American Journal of Physiology*, 263:R164–R168 (1992).

Additionally, high levels of glucocorticoid production have been observed in males infected with the human immunodeficiency virus (HIV). Excessive glucocorticoid production was observed in both HIV-positive and early AIDS individuals. See J. M. Villette et al., "Circadian Variations in Plasma Levels of Hypophyseal, Adrenocortical and Testicular Hormones in Men Infected with Human Immunodeficiency Virus," *J. Clin. Endocrinol. Metab.*, 70:572–577 (1990). During HIV infection, chronic renal failure which progresses very rapidly is a common occurrence and may be accelerated by sustained high levels of glucocorticoid production. It is contemplated that the glucocorticoid clamp of the method of the present invention will also be useful for slowing the progression of chronic renal failure in patients diagnosed with HIV nephropathy.

In order to demonstrate the effect of the administration of agents which suppress glucocorticoid action together with a glucocorticoid, a clinical study was conducted as described below.

Clinical Test Methods

Linear regression analysis of glomerular filtration rate (GFR) as a function of time before and after treatment with a combination of ketoconazole and prednisone was performed. Four patients (#36, #37, #40, #52) with chronic renal failure were included in the study. Patient #36 was a 35-year old white male diagnosed with chronic glomerulonephritis; Patient #37 was a 35-year old white male diagnosed with type I diabetes; Patient #40 was a 54-year old white male diagnosed with interstitial nephritis; and Patient #52 was a 72-year old white male diagnosed with IgA nephropathy.

In the studies, the subjects received 200–400 mg of ketoconazole and 2.5 mg of prednisone daily. The replacement dose level of prednisone is about 5 to about 8 mg/day. Ketoconazole, sold under the trademark "NIZORAL" was obtained from Janssen Pharmaceutica, Inc of Piscataway, N.J. All four patients received the combination for at least 3½ months.

Glomerular filtration rate (GFR) was measured bi-monthly as the urinary clearance of intravenously injected $^{99m}$Tc-DTPA (100 uCi). Three collection periods were averaged. Correction for body weight or surface area was not made. Progression was calculated as the linear regression of GFR on time in months. Pretreatment values were employed.

Results of Clinical Tests

The data were analyzed by linear regression analysis. FIGS. 1A, 1B, 1C and 1D are graphs of the sequential values for GFR for patients #36, #37, #40 and #52, respectively.

Figure 1D:
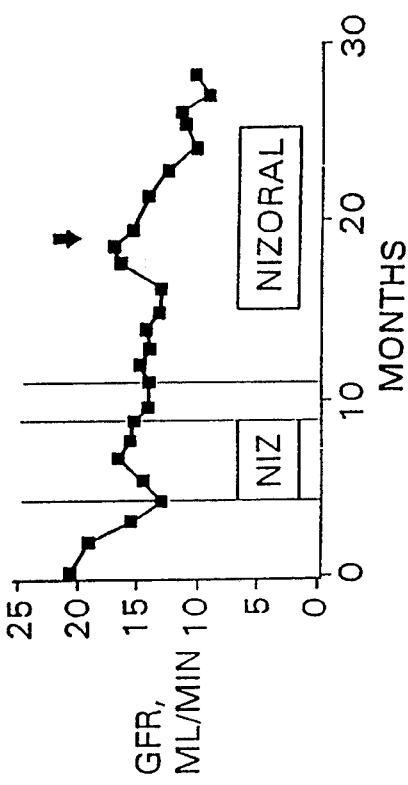
Figure 1A:
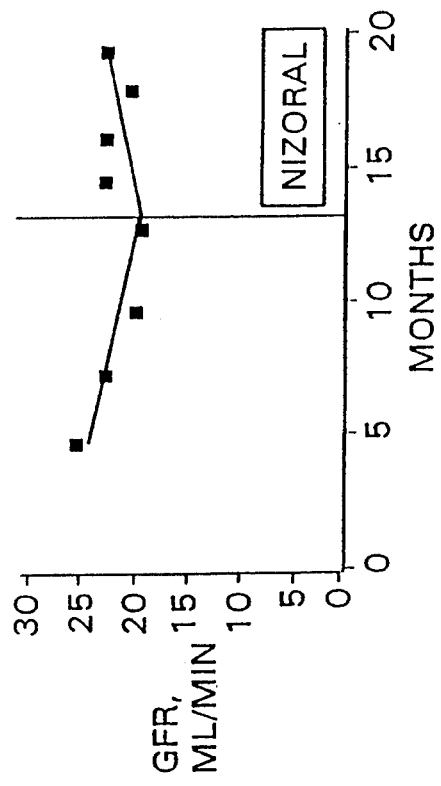

FIG. 1A shows the course of progression of Patient #36 (chronic glomerulonephritis) during a 13-month pretreatment phase and an approximately 6-month treatment phase where 400 mg "NIZORAL" and 2.5 mg prednisone were administered daily. The graph shows that treatment with "NIZORAL" and prednisone appears to have reversed the progression of renal failure.

FIG. 1B shows the course of progression of Patient #37 (Type I diabetes) during a 4.5-month pretreatment phase and a 3.5-month treatment phase where 200–400 mg "NIZORAL" and 2.5 mg prednisone were administered daily. The graph shows a retarding of renal failure progression in an insulin-dependent diabetic. This patient was losing function extremely rapidly (approximately 1.8 ml/min/month) in the pretreatment period.

Figure 1C:
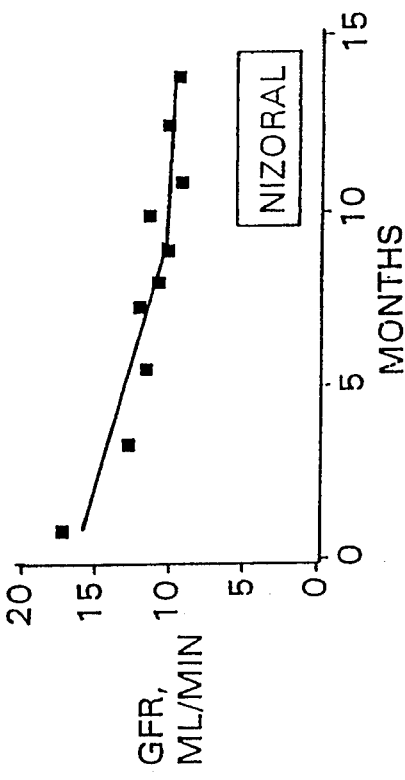

FIG. 1C shows the progression of Patient #40 (interstitial nephritis) during a 9-month pretreatment phase and an approximately 5-month treatment phase where 400 mg "NIZORAL" and 2.5 mg prednisone were administered daily. The graph shows a retardation of progression in this patient.

FIG. 1D shows the course of progression of Patient #52 (IgA nephropathy) during an approximately 4-month pretreatment phase and an approximately 2-year treatment phase where 400 mg "NIZORAL" and 2.5 mg prednisone were administered daily. Therapy was discontinued for approximately two months and then restarted. The patient lost some renal function during a period when the prednisone dose had to be increased to 10 mg/day to control a recurrence of polymyalgia (indicated on the graph by an arrow). Extrapolating from the decrease in GFR of this patient in the pretreatment phase, it is likely that dialysis would have been necessary beginning approximately around month eight of his study. Thus, dialysis has already been deferred about 20 months.

A causal relationship between retardation or arrest of the progression of chronic renal failure and administration of a glucocorticoid suppressor together with a glucocorticoid in patients with chronic renal failure is strongly suggested by these data. Therefore, it is believed that other agents and measures that suppress the production of glucocorticoids administered together with a dose of prednisone or another glucocorticoid should slow or arrest progression of chronic renal failure.

The present invention may be embodied in other specific forms without departing from the spirit or essential attributes thereof and, accordingly, reference should be made to the appended claims, rather than to the foregoing specification as indicating the scope of the invention.

I claim:

1. A method of retarding the progression of chronic renal failure in humans comprising administering to the human suffering from chronic renal failure an effective amount of an agent which suppresses the production of glucocorticoids together with an effective amount of glucocorticoid., said agent excluding opioids.

2. The method according to claim 1, wherein the agent which suppresses the production of glucocorticoids and the glucocorticoid are administered orally.

3. The method according to claim 1, wherein the agent which suppresses the production of glucocorticoids is selected from the group consisting of ketoconazole, sodium valproate, enkephalins and their synthetic analogs, clonidine and oxytocin.

4. The method of claim 1, wherein the effective amount of the glucocorticoid is less than the replacement dose level.

5. The method according to claim 1, wherein the agent which suppresses the production of glucocorticoids is ketoconazole.

6. The method of claim 5, wherein the ketoconazole is administered in an amount of about 200 to about 400 mg/day.

7. The method according to claim 1, wherein the glucocorticoid is prednisone.

8. The method of claim 7, wherein the prednisone is administered in an amount of about 2.5 mg/day.

9. A method of retarding the progression of chronic renal failure in humans comprising administering to the human suffering from chronic renal failure an effective amount of ketoconazole together with an amount of prednisone less than the replacement dose level.

10. The method according to claim 9, wherein the ketoconazole is administered in an amount of about 200 to about 400 mg/day and the prednisone is administered in an amount of about 2.5 mg/day.

11. The method according to claim 9, wherein the ketoconazole and the prednisone are administered orally.

12. The method according to claim 1, wherein the chronic renal failure results from human immunodeficiency virus nephropathy.

13. The method according to claim 1, wherein the chronic renal failure results from chronic glomerulonephritis.

14. The method according to claim 1, wherein the chronic renal failure results from type I diabetes.

15. The method according to claim 1, wherein the chronic renal failure results from interstitial nephritis.

16. The method according to claim 1, wherein the chronic renal failure results from IgA nephropathy.

* * * * *